United States Patent
Lazik et al.

(10) Patent No.: US 6,679,096 B1
(45) Date of Patent: Jan. 20, 2004

(54) METHOD FOR THE MEASUREMENT OF THE CONCENTRATION OR THE PARTIAL PRESSURE OF GASES IN FLUIDS IN GAS SENSOR

(76) Inventors: Detlef Lazik, Kirchstr. 7, 06198 Salzmünde (DE); Helmut Geistlinger, Simsonstr. 9, 04107 Leipzig (DE)

( * ) Notice: Subject to any disclaimer, the term of this patent is extended or adjusted under 35 U.S.C. 154(b) by 0 days.

(21) Appl. No.: 09/762,061
(22) PCT Filed: Jun. 2, 2000
(86) PCT No.: PCT/EP00/05081
§ 371 (c)(1),
(2), (4) Date: Apr. 11, 2001
(87) PCT Pub. No.: WO01/53796
PCT Pub. Date: Jul. 26, 2001

(30) Foreign Application Priority Data
Jun. 1, 1999 (DE) .......................... 199 25 842

(51) Int. Cl.$^7$ .................. G01N 7/00; G01N 33/18; G01N 33/497
(52) U.S. Cl. ........... 73/19.01; 73/19.05; 73/19.1; 73/19.12
(58) Field of Search .............. 73/19.01, 19.05, 73/19.06, 19.1, 19.12; 600/364

(56) References Cited

U.S. PATENT DOCUMENTS

| | | | |
|---|---|---|---|
| 3,871,228 A | | 3/1975 | Weiss |
| 3,929,003 A | * | 12/1975 | LLewellyn ............ 73/19.01 |
| 4,016,864 A | * | 4/1977 | Sielaff et al. ......... 422/103 |
| 4,112,737 A | | 9/1978 | Morgan |
| 4,516,580 A | * | 5/1985 | Polanyi ............... 210/321.63 |
| 4,550,590 A | * | 11/1985 | Kesson ............... 73/19.05 |
| 4,662,210 A | | 5/1987 | D Aoust |
| 5,121,627 A | * | 6/1992 | D'Aoust .............. 73/19.05 |
| 5,331,845 A | * | 7/1994 | Bals et al. ........... 73/19.1 |
| 5,333,609 A | * | 8/1994 | Bedingham et al. .... 600/339 |
| 5,617,850 A | * | 4/1997 | Pontzer ............... 600/364 |
| 5,763,762 A | | 6/1998 | Sweeney |
| 6,003,362 A | * | 12/1999 | Dieckmann et al. ..... 356/43 |

FOREIGN PATENT DOCUMENTS

| | | | |
|---|---|---|---|
| DE | 2926138 A | * | 1/1981 |
| EP | 429397 A2 | * | 5/1991 |

* cited by examiner

Primary Examiner—Edward Lefkowitz
Assistant Examiner—Michael Cygan
(74) Attorney, Agent, or Firm—Birch, Stewart, Kolasch & Birch, LLP

(57) ABSTRACT

A method measures the concentration of the partial pressure of gases, particularly oxygen, in fluids. Know methods for measurements under rough conditions, e.g., measurement of the oxygen partial pressure in grounds, dumps or in the ground water are completely unsuitable. In the present method as described, in the internal area of a hollow vessel closed off to the outside, whose wall consists at least partially of a gas-specific permeable synthetic material that is in contact with the fluid with its external side, the partial pressure change proportional to the gas concentration is measured as a time-scanning of pressure change or as a change of a pressure-dependent physical variable. The measuring principle is very simple and is particularly suitable for the determination and long-time monitoring of the oxygen concentration and of further gases and can also be used in problematic locations.

9 Claims, 2 Drawing Sheets

METHOD FOR THE MEASUREMENT OF THE CONCENTRATION OR THE PARTIAL PRESSURE OF GASES IN FLUIDS IN GAS SENSOR

This application is the national phase under 35 U.S.C. §371 of PCT International Application No. PCT/EP00/05081 which has an International filing date of Jun. 2, 2000, which designated the United States of America.

FIELD OF THE INVENTION

The invention concerns a method for the measurement of the concentration or the partial pressures of gases, particularly oxygen, in fluids as well as a gas sensor for its execution. The measurement of the concentration of oxygen or other gases is of major significance in various fields of engineering, such as in chemical processing, environmental and medical technology etc.

DESCRIPTION OF THE PRIOR ART

Traditionally, dissolved oxygen is measured galvanically, polarographically or potentiometrically in electrochemical measuring cells according to the Clark principle, meaning, the current is measured as a function of the time or of the potential or the potential in the zero current state in an electrolyte between a cathode and an anode.

In order to conduct oxygen into the measuring cell inner zone, a membrane is located which is permeable to oxygen and to gas, respectively, and this membrane separates the electrolyte in the measuring cell from the fluid to be measured.

The measurement presupposes the equilibrium setting of the partial pressures outside and inside the cell, and/or the concentrations corresponding with it by way of the Henry constant. As the electrochemical reaction consumes oxygen, a constant forward flow must be produced by stirring the measuring cell in the fluid. For this reason, many manufacturers offer mountable stirring mechanisms. Further methods are also known which compensate the oxygen consumption and, therefore, are only suitable for the measurement of low concentrations or/and in small volumes. The measuring values must be pressure-compensated, and corrected with regard to salinity and temperature.

The measurement is locally defined at the location of the sensor. Problems easily occur as a result of contamination at the relatively small membrane as well as air inclusions during the change of membranes.

There are other possibilities of oxygen measurement, for example, in the evaluation of the oxygen-concentration-dependent modulation of the phase radiant light received.

For the concentration measurement of other gases, gas-specific methods are known, insofar as recourse is not made to gas chromatography.

All methods mentioned require a complicated and sensitive sensor technology. For this reason appropriate measuring equipment is expensive and has only a low service life and/or requires high expenditure with regard to maintenance and calibration. For measurements under rough conditions, for example the measurement of oxygen partial pressure in low stratums, they are completely unsuitable.

In deeper stratums, such as in the ground water, gas measurement has not been possible up to the present time, the reason being that a measurement could only be carried out by means of a sample extraction. As the water is under a correspondingly high pressure and has a special temperature, degasification would occur at sample extraction and measurement under atmospheric conditions and no measuring values allocatable to the location of measurement would be obtained. Moreover, local measurement would seem problematic because it is not possible to estimate which disturbance affects the system during sample extraction.

BRIEF SUMMARY OF THE INVENTION

The invention is based on the task assignment of stating a method and a suitable gas sensor of the category described in the introduction, which work in an uncomplicated manner and with simple means, which are sturdy and which lead to representative results for the structure under examination.

It was discovered with surprise that the properties of oxygen-permeable synthetic materials such as e.g. PTFE or other gas-specific permeable synthetic materials can be used for building up an oxygen and gas sensor, respectively, which allows the determination of the partial pressure or the concentration of the oxygen or other gases of a gas mixture by means of direct pressure measurement because the partial pressure to be measured within a random fluid causes an equivalent pressure in an enclosed vessel whose wall consists at least partially of such a synthetic material permeable to oxygen and/or gas.

PTFE (polytetrafluoroethylene) and PTFE-similar products such as Teflon, a copolymer of PTFE and <5 mol-% PAVE (perfluoro alkyl vinyl ether), have a relatively high permeability for oxygen. At the same time, PTFE has an outstanding significance among the synthetic materials because of its enormous resistance and stability opposite random influences from its ambient surroundings. Adhesion and cohesion of the material are very low. Subsequently, the frictional forces also are reduced to a correspondingly low level. The surfaces remain clean.

PTFE has a further remarkable property. The permeability of the synthetic material, e.g. opposite the good water-soluble carbon dioxide and the nitrogen mainly prevailing in the atmosphere, lies two orders of magnitude below that of other synthetic materials such as, for example, HDPE (high density polyethylene).

The utilization of the properties relatively high oxygen permeability and negligible permeability opposite other liquids and gases with the gas sensor built up according to the invention leads to the result that the partial pressure of the oxygen in a mixture of substances causes an equivalent partial pressure in a closed Teflon vessel and that this, independent of the absolute pressure existing in the vessel and only dependent on the oxygen partial pressure prevailing beforehand in the vessel, causes a change of the absolute pressure. This means that the measurement of the oxygen concentration can be reduced to a simple pressure measurement.

The method can be applied to any random fluid media.

The pressure is measured by means of, for example, measuring sensors which have longtime and overload stability but which are also almost to a randomly small degree dimensionable and are linear in a wide range, such sensors being on the basis of monocrystal silicium and having an accuracy of approximately 0.4%. With this, the possibility of an inexpensive and precise oxygen partial pressure measurement can be assumed where the concentration is determined, depending on the peripheral and initial conditions of the measurement, both from the rising speed of the pressure with known material properties of the applied synthetic material as well as from the geometry of the measuring cell or—without this knowledge—as a function of the absolute pressure difference.

A further variant exists in the measurement by means of differential pressure transmitters against a reference vessel which is subject to known conditions, e.g. atmospheric conditions, and which is otherwise configured as similar as possible to the measuring system, meaning, in particular with reference to material selection of the measuring vessel and its dimensions.

Water vapor also diffuses through the wall of the vessel, as well as further gases albeit with larger time constants. For this reason, a calibration is performed before a measurement is carried out again where the vessel is purged with nitrogen or a gas mixture with a known composition and/or air. With a tempering of the purging gas, a certain measuring temperature can, if required, be set simultaneously in the vessel.

The measuring cell structural arrangement and the measuring principle can be adapted to the individual measuring problem in question. In the simplest case, the gas sensor consists of a hollow body whose wall is at least partially formed by means of an oxygen-permeable membrane and in which a pressure probe is arranged. In addition to this point-type measurement (e.g., also in spherical-shaped geometry of the measuring cell), and with the assistance of a hose-type measuring arrangement, the integrating measurement along a line or, with the assistance of a hose network, the integrating measurement of a surface is also possible at all times. With this, an essential objective within monitoring task assignments in the environment—the determination of oxygen in the ground air or in the ground water of heterogeneous systems—is obtained in a simple and representative manner.

In general, only point-type and qualitative in situ gas monitoring has been possible up to the present. As already determined above, the isochore time-scanning of pressure change registered at the measuring sensor is the result of locally limited diffusion actions if and when the pressure equalization in a measuring hose is fast opposite the locally different equalization actions of the partial pressure. The pressure measurement in such a measuring hose therefore integrates by way of all locally limited partial pressure changes, where the substance to be measured is not in immediate contact with the measuring sensor, meaning, the pressure sensor. If a concentration gradient for oxygen to the gas mixture exists at any random contact location of the outer zone with the collecting line, it leads to an increase of the oxygen partial pressure inside the hose as a result of the oxygen diffusion. This partial pressure increase at the sample extraction location is measured at the measuring location as an overall pressure increase. The increased oxygen partial pressure does not have to exist at the measuring location, meaning, at the pressure sensor itself.

Therefore, a certain quantity of oxygen molecules does not have to exist at the location of the measuring sensor because the pressure and the pressure change are intensive state variables which propagate at sound velocity in the gas mixture in the internal zone of a hose and are therefore independent of the location within a closed system. The time resolution of the measuring systems is therefore determined only by the relatively slow diffusion kinetics into the measuring line.

For the in situ measurement the measuring vessel, e.g. a hose-shaped measuring line, can be solidly installed in the examination object and does not require any maintenance in this location.

A possibility for spatial limitation of the reference point(s) for the measuring is to make the collecting line gas-selective in certain areas only. The rest of the line can then be made of e.g. a high quality steel capillary.

The equation of state of the ideal gas $p*V/T=$const. applies, in good proximity, for gases in closed systems and under atmospheric pressure. At constant temperature, therefore, and instead of an isochore time-scanning of pressure change, the isobaric volume change or the product of pressure and volume change can be adopted for measurement. Both variables provide immediately the gas volume change as a function of time where the measurement under isobaric conditions is easier to interpret from a mathematical viewpoint. An additional gas-tight line can serve the purpose of determining the mean temperature.

If suitable collecting lines or networks are applied, at differential heights as required, to waste dumps, bioreactors and similar objects in order to measure, for example, oxygen distribution during aerobic degradation of organic pollutants, then the integral measuring principle is practically ideal for this application purpose.

A hose bundle with different materials provides a differentiated time behaviour of pressure or volume changes where the essential -and first change always occurs by the selectively preferred gas, however subordinating itself to the diffusion of the other gases in the ratio of the diffusion constants. A large number of such materials with different gas selectivity is known. For a hose number of the bundle which is equal to the number of the expected gases, and/or the gases to be measured, plus an additional hose as required, a simply solvable and certain equation system leads to the determination of representative partial pressure of the gases and the temperature in the ambient surroundings of the hose bundle which contains as material parameters the diffusion constants $D_{ij}$ and the temperature conductivity $\lambda_j$, the geometry of the hoses (length $L_j$, diameter $2R_j$ wall thickness $b_j$ of the hoses) and the measuring variables pressure $p_j$ (t) or volume $V_{j(t)}$ (index I for gases, index j for hose).

A further application possibility are the area representative gas tracer tests for the purpose of determining the gas migration in the subsurface of the ground over parallel laid hose bundles for water-saturated and unsaturated conditions. In this case, for example, and by means of the combination of inert and reactive gases, the gas consumption as a result of microbic reaction or other gas consuming processes can be cumulatively determined and is available as a reliable variable for the thermodynamic interpretation of reactions in the subsurface.

The measuring principle is suitable for determining the oxygen concentration, also of further gases if required, and also in such locations where such a measurement had previously met with great problems, meaning, for example the direct measurement in the ground in greater depths or the direct measurement in waste waters and flowing waters.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

As follows, the invention is explained in greater detail of the basis of an embodiment. The relevant drawings, which are given by way of illustration only, and thus are not limitative of the present invention, and show the following items.

DETAILED DESCRIPTION OF THE INVENTION

Figure 1:
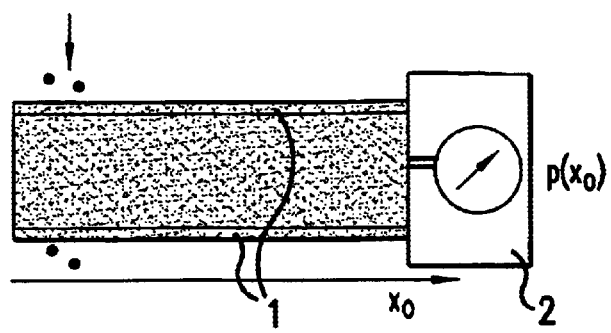
FIG. 1 a schematic illustration of a gas sensor according to the invention.
Figure 4:
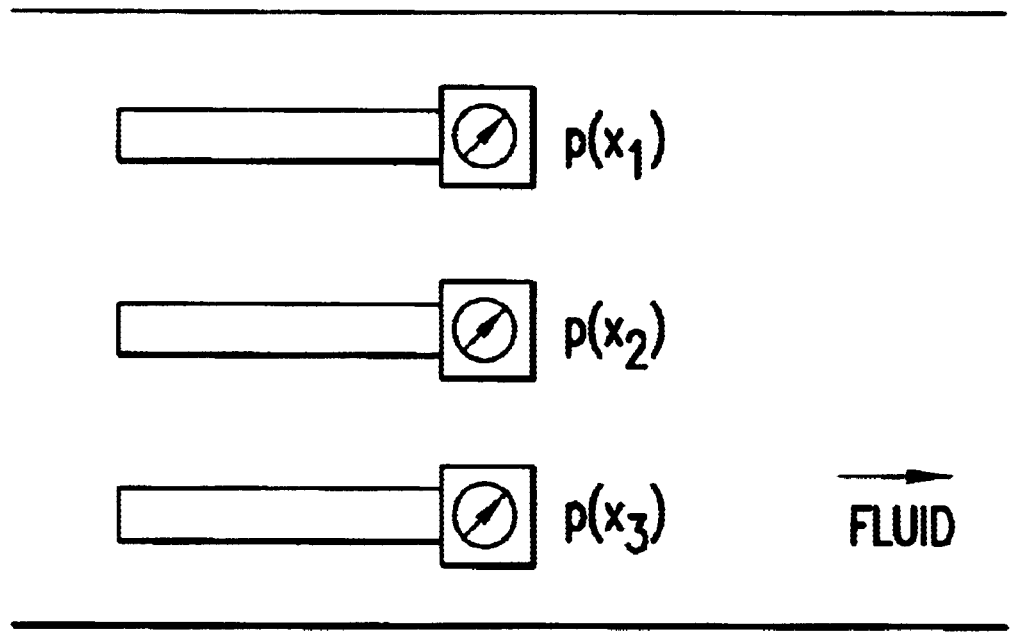
FIG. 4 the gas sensor with several vessels.

FIG. 1 shows a gas sensor for determining the oxygen concentration of a fluid. It consists of a hose with a hose wall 1 made of PTFE which, in the cast as presented here, is closed off on one side. It could otherwise also be built up as a ring. Over its entire length x, it is able to allow the diffusion of oxygen from a fluid, for example for the measurement of oxygen concentration in the water within a ground layer. A pressure sensor 2 is located at the hose end. A plurality of vessels or hoses 1 can be used as see in FIG. 4.

The absolute pressure measured with the pressure sensor 2 or the rise of the pressure change are a measure for the oxygen partial pressure in the fluid to be measured.

Figure 2:
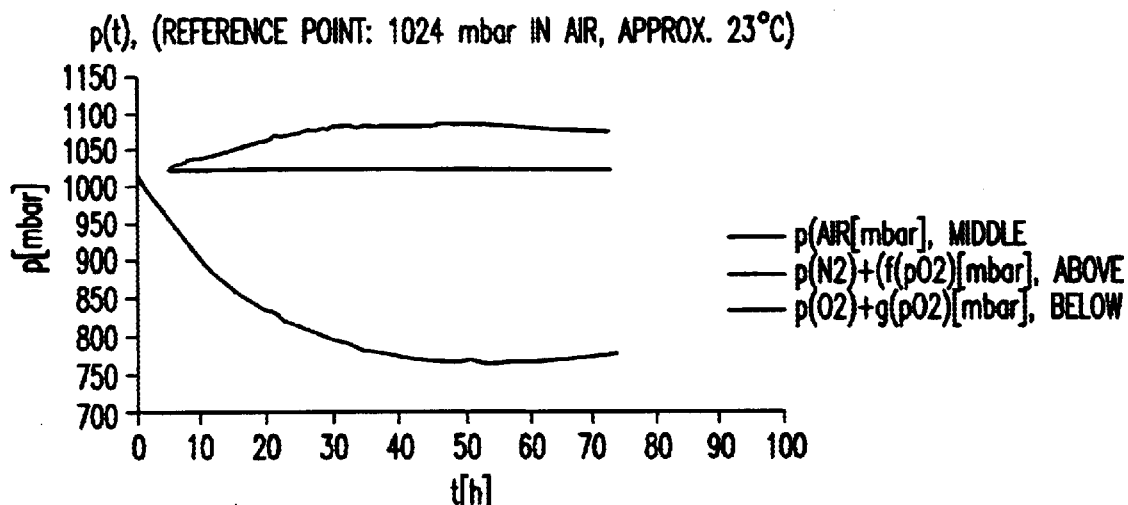
FIG. 2 the pressure pattern in the vessel of the gas sensor in an experiment.
Figure 3:
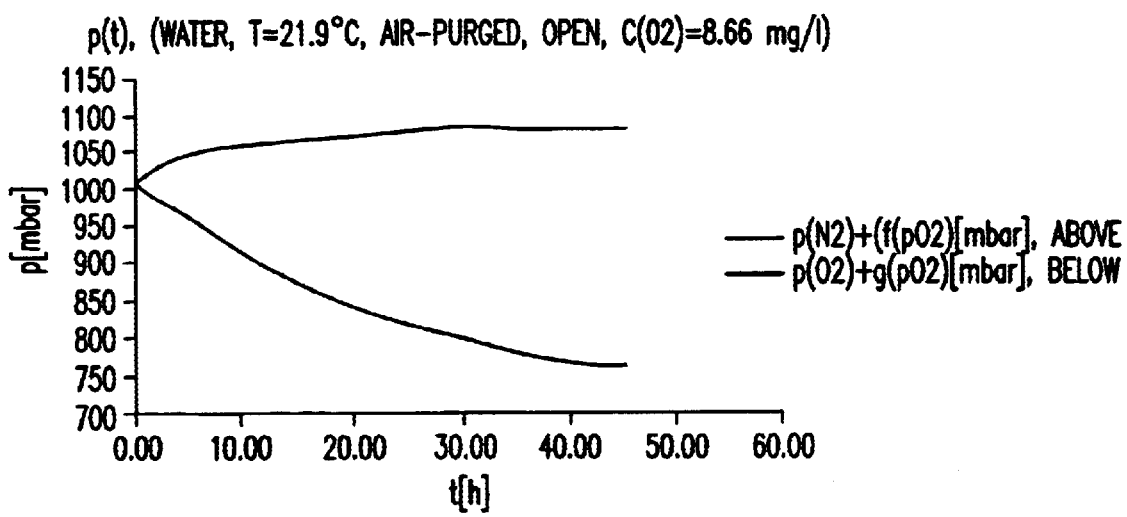
FIG. 3 the pressure pattern in a further experiment.

For the functional verification of the gas sensor with this structural arrangement, four experiments were performed, the results of which are shown in FIG. 2 and in FIG. 3.

A Teflon hose filled with nitrogen was selectively subjected to air-purged water and air at an initial internal and external pressure of P=1024 mbar. A pressure probe was installed at the hose end. The absolute pressure was recorded as a time function. The oxygen partial pressure outside the hose caused a pressure rise in the Teflon hose in both cases which increased significantly above the ambient pressure (upper curves in FIG. 2 and FIG. 3).

A Teflon hose filled with oxygen under a pressure of P=1024 mbar was selectively subjected to air-purged water and air. A pressure probe was again installed at the hose end and the pressure recorded as a time function. The oxygen partial pressure existing within the hose, increased with reference to the ambient surroundings, caused in these two cases a pressure drop in the Teflon hose, meaning, the hose internal pressure dropped significantly below the ambient pressure corresponding to the diffusion of the oxygen molecules to the outside, as dependent on the partial pressure gradient (lower curves in FIG. 2 and FIG. 3).

Relatively thick-walled Teflon hoses with an internal diameter of >5 mm were applied here because the tests were purely demonstrational. Subsequently, the obtained pressure functions p=p (t) indicate relatively high time constants. For real measuring task assignments, correspondingly smaller time constants can be achieved with thin-walled hoses at a smaller volume/surface-ratio. On the other hand, the wall thickness of the hose can be deliberately selected for the purpose of suppression of short-wave fluctuations of the partial pressure of oxygen.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for the measurement of concentration or partial pressure of gases in fluids wherein in an internal area of a hollow vessel closed off to the outside, whose wall is at least partially made of a single gas component-specific permeable synthetic material, an exterior of which is in contact with the fluid, the partial pressure change proportional to the gas concentration is measured as a time-scanning of pressure change or as a change of a pressure-dependent physical variable, the pressure measurement being carried out in several vessels which are in contact with the fluid and which have varying gas permeability, and the timing behavior of the measuring values for determining the concentration of several gases in the fluid being set in relationship to one another in an equation system.

2. The method according to claim 1, wherein the vessel, before a measurement, is purged with a gas or gas mixture having a known composition.

3. The method according to claim 2, wherein the vessel, before a measurement, is purged with nitrogen.

4. The method according to claim 2, wherein temperature of the gas or gas mixture is set in accordance with the measuring conditions.

5. The method according to claim 1, wherein the pressure measured in each case in the vessel is set in relationship to a similar reference system which is subject to known conditions.

6. A single component gas sensor for measurement of concentration or partial pressure of gases in fluids, comprising a plurality of hollow vessels, closed off to the outside, each having at least a partially oxygen- or single gas component-specific permselective synthetic material, an exterior of the walls being contactable with the fluid and a partial pressure change proportional to the gas concentration being measured as a time-scanning of pressure change or as a change of a pressure-dependent physical variable by a pressure sensor which measures the internal pressure in the vessel for determining the concentration of several gases in the fluid being set in relationship to one another in an equation system.

7. The single component gas sensor according to claim 6, wherein the synthetic materials are presented in the form of different membranes which tightly seal off the vessels.

8. The single component gas sensor according to claim 6, wherein the synthetic materials are presented in the form of hoses tightly bound to the remaining parts of the vessels.

9. The single component gas sensor according to claim 6, wherein the synthetic materials are presented in the form of hose networks tightly bound to the remaining parts of the vessels.

* * * * *